US00PP27523P2

(12) United States Plant Patent
Lee

(10) Patent No.: US PP27,523 P2
(45) Date of Patent: Jan. 3, 2017

(54) AZALEA PLANT NAMED 'LAZAMORED'

(50) Latin Name: ***Rhododendron* hybrid**
Varietal Denomination: Lazamored

(71) Applicant: Robert Edward Lee, Independence, LA (US)

(72) Inventor: Robert Edward Lee, Independence, LA (US)

(73) Assignees: Robert Edward Lee, Independence, LA (US); Plant Development Services, Inc., Loxley, AL (US)

( * ) Notice: Subject to any disclaimer, the term of this patent is extended or adjusted under 35 U.S.C. 154(b) by 0 days.

(21) Appl. No.: 14/756,221

(22) Filed: Aug. 18, 2015

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Susan McCormick Ewoldt
(74) *Attorney, Agent, or Firm* — Audrey Charles

(57) ABSTRACT

A new and distinct cultivar of Azalea plant named 'Lazamored', characterized by its medium red-orange colored flowers, dark green-colored foliage, moderately vigorous, upright-mounded growth habit and strong multi-seasonal reblooming, is disclosed.

1 Drawing Sheet

Latin name of genus and species of plant claimed: *Rhododendron* hybrid.

Variety denomination: 'Lazamored'.

BACKGROUND OF THE INVENTION

The present invention relates to a new and distinct cultivar of Azalea plant botanically known as *Rhododendron* hybrid and hereinafter referred to by the cultivar name 'Lazamored'.

The new cultivar originated in a controlled breeding program in Independence, La. during the spring of 2006. The objective of the breeding program was the development of Azalea cultivars with attractive flower color with multi-seasonal blooming and that perform well in the garden.

The new Azalea cultivar is the result of cross-pollination. The female (seed) parent of the new cultivar is 'Red Slippers', not patented, characterized by its medium red-colored flowers, dark green-colored foliage, and vigorous, semi-upright growth habit. The male (pollen) parent of the new cultivar is 'Arabesk', not patented, characterized by its dark red-colored flowers, dark green-colored foliage, low growth vigor and compact growth habit. The new cultivar was discovered and selected as a single flowering plant within the progeny of the above stated cross-pollination during September 2007 in a controlled environment in Independence, La.

Asexual reproduction of the new cultivar by terminal stem cuttings since September 2007 in Independence, La. and later in Loxley, Ala. and Irvington, Ala. has demonstrated that the new cultivar reproduces true to type with all of the characteristics, as herein described, firmly fixed and retained through successive generations of such asexual propagation.

The following characteristics of the new cultivar have been repeatedly observed and can be used to distinguish 'Lazamored' as a new and distinct cultivar of Azalea plant:

1. Medium red-orange colored flowers;
2. Dark green-colored foliage;

3. Moderately vigorous, upright-mounded growth habit; and
4. Strong multi-seasonal reblooming.

Plants of the new cultivar differ from plants of the female and male parents primarily in having strong repeat blooming. In addition, plants of the new cultivar differ from the female parent in having reduced growth vigor and a different growth habit and from the male parent in having a different shade of red flower color.

Of the many commercially available Azalea cultivars, the most similar in comparison to the new cultivar is Autumn Cheer 'Conlef', U.S. Plant Pat. No. 10,579. However, in side by side comparisons, plants of the new cultivar differ from plants of 'Conlef' in at least the following characteristics:

1. Plants of the new cultivar have a flower color different from plants of 'Conlef';
2. Plants of the new cultivar have a larger corolla diameter than plants of 'Conlef'; and
3. Plants of the new cultivar have a leaf color different from plants of 'Conlef'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Lazamored'. The plants were grown in 2-gallon containers for 9 months outdoors in Irvington, Ala. Plants were given one pinch at transplant.

DETAILED BOTANICAL DESCRIPTION

Figure 1:
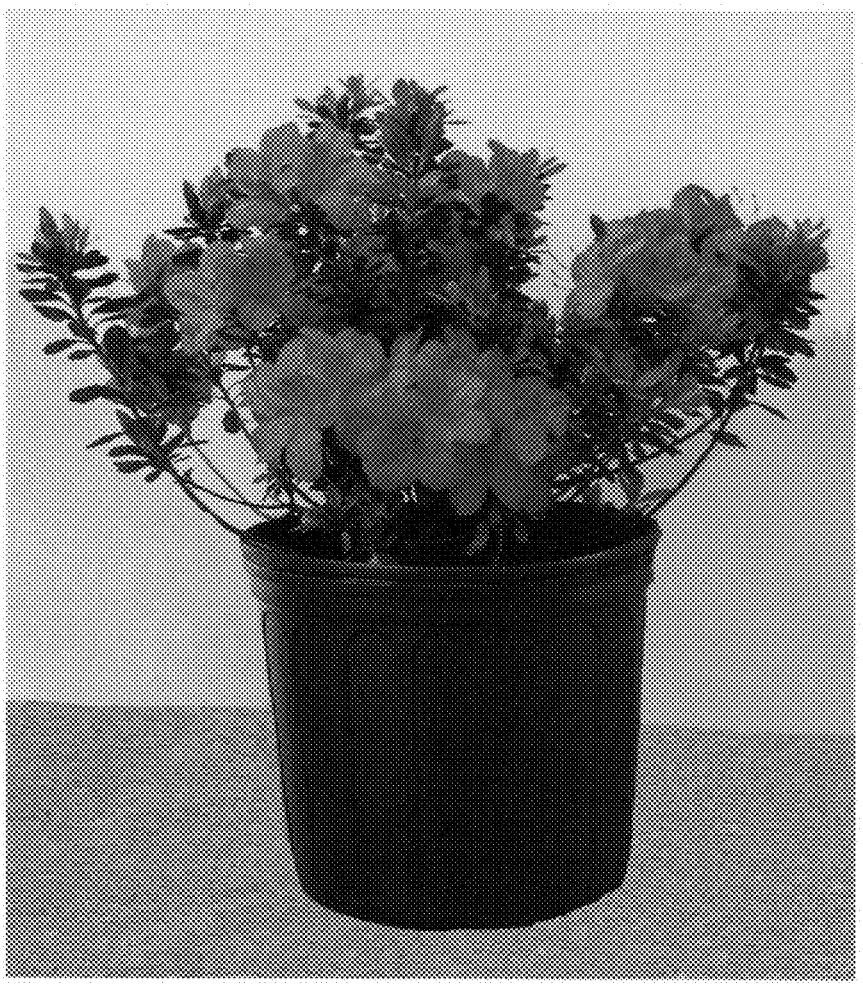
FIG. 1 illustrates a side view of the overall growth and flowering habit of 'Lazamored'.
Figure 2:
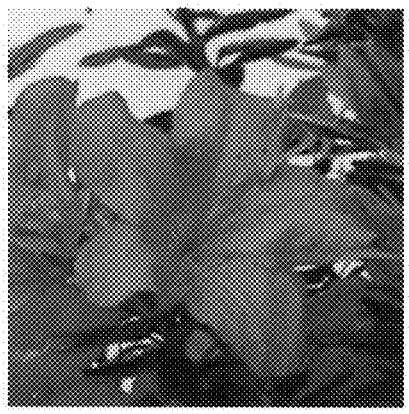
FIG. 2 illustrates a close-up view of an individual flower of 'Lazamored'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2015 under natural light conditions in West Chicago, Ill.

The chart used in the identification of colors described herein is The R.H.S. Colour Chart of The Royal Horticultural Society, London, England, 2007 edition, except where general color terms of ordinary significance are used. The color values were determined in April 2015 under natural light conditions in West Chicago, Ill.

The following descriptions and measurements describe plants produced from semi-hardwood stem cuttings from stock plants. Rooted plants, liners, were transplanted into 2-gallon containers utilizing a soilless growth medium. Plants were given one pinch at transplant and grown for approximately 9 months outside in Irvington, Ala. under conditions comparable to those used in commercial practice. Average winter temperatures ranged from 63° F. to 42° F. (17° C. to 5° C.) and average summer temperatures ranged from 91° F. to 72° F. (33° C. to 22° C.). Measurements and numerical values represent averages of typical plants.

Botanical classification: *Rhododendron* hybrid cultivar Lazamored.

Parentage:

*Female parent*.—'Red Slippers', not patented.

*Male parent*.—'Arabesk', not patented.

Propagation:

*Type cutting*.—Semi-hardwood stem cuttings.

*Time to initiate roots, summer*.—Approximately 25 to 30 days.

*Time to produce a rooted cutting, summer*.—Approximately 60 to 70 days.

*Root description*.—Fine, fibrous; initially white in color becoming light brown with age.

*Rooting habit*.—Freely branching, dense.

Plant description:

*Commercial crop time*.—Approximately 10 months from a rooted cutting to finish in a 1-gallon container.

*Growth habit and general appearance*.—Perennial, evergreen flowering subshrub; moderately vigorous, upright-mounded growth habit.

*Size*.—Height from soil level: Approximately 40.0 cm. Width: Approximately 58.0 cm.

*Branching habit*.—One main trunk, freely branching, pinching improves lateral branching. Quantity of primary lateral branches per plant: Approximately 9. Quantity of secondary lateral branches: Approximately 2 to 8 per primary branch.

*Primary lateral branches*.—Strength: Very strong, rigid. Length: Approximately 27.0 cm. Diameter at midpoint: Approximately 7.0 mm. Texture: Woody, rough. Color: 200A to 200B.

*Secondary lateral branches*.—Strength: Very strong, somewhat flexible. Length: Approximately 26.5 cm. Diameter at midpoint: Approximately 4.0 mm. Length of central internode: Approximately 1.1 cm. Texture: Densely pubescent, hairs appressed. Color of young branches: 145A and N144A heavily tinted with 187B to 187C. Color of mature branches: N199B with 200A.

Foliage description:

*General description*.—Leaf retention: Very good winter leaf retention. Fragrance: None detected. Form: Simple. Arrangement on flowering stem: Alternate.

*Leaves*.—Aspect: Acute angle to stem, blades extend downward with age. Shape: Elliptic to obovate. Margin: Entire. Apex: Acute, mucronulate. Base: Broadly attenuate. Venation pattern: Pinnate, finely reticulate. Length of mature leaf: Approximately 3.3 cm. Width of mature leaf: Approximately 1.8 cm. Texture of upper and lower surfaces: Moderately pubescent, hairs appressed, leathery. Color of upper surface of young foliage: 137A with venation of 146D or indistinguishable from leaf surface. Color of lower surface of young foliage: Closest to 138B with venation of 146D or indistinguishable from leaf surface. Color of upper surface of mature foliage: N137A heavily tinted with 187A and with venation of 187A or indistinguishable from leaf surface. Color of lower surface of mature foliage: Closest to 146B tinted with 187A and with venation of 187A or indistinguishable from leaf surface.

*Petiole*.—Length: Approximately 5.0 mm. Width: Approximately 2.0 mm. Texture: Densely pubescent, hairs appressed. Color: 146C tinted with 187A, darkens to 187A with age.

Flowering description:

*Flowering habit*.—'Lazamored' flowers in spring from early March to mid-April and then remontant flowering during spring and autumn.

*Lastingness of individual flower on the plant*.—Flowers are durable and long- lasting; depending on the temperature flowers can last approximately one week on the plant.

Flower description:

*General description*.—Type: Single, open funnel-shaped, non-persistent. Arrangement: Terminal clusters of 1 to 5 flowers and buds in whorls, approximately 25 clusters per plant. Fragrance: None detected.

*Bud*.—Rate of opening: Generally takes 2 to 3 days for bud to progress from first color to fully open flower.

*Bud just before opening*.—Shape: Obovoid. Length: Approximately 2.2 cm. Diameter: Approximately 9.0 mm. Texture: Glabrous. Color: N34A.

*Corolla*.—Length: Approximately 7.7 cm. Width: Approximately 8.0 cm. Depth: Approximately 4.0 cm.

*Petals*.—Quantity: 5 to 6, fused to form a tube that extends 3.0 cm from the base to the free portions between the upper and lateral petals and extends 1.7 cm to 2.0 cm from the base to the free portions of the lower petals, unfused portions imbricate. Shape: Obovate. Appearance: Velvety. Margin: Entire, undulate. Apex: Obtuse. Length of free portion: Approximately 3.0 cm. Width: Approximately 2.8 cm to 3.0 cm. Texture of upper surface: Glabrous, tube portion densely pubescent with very short hairs. Texture of lower surface: Glabrous. Color of upper surface when first and fully open: N34B and N34C with speckles of 60A on upper and lateral petals. Color of lower surface when first and fully open: N34C with centers of N34D.

*Sepals*.—Quantity per flower: 5, fused at base. Shape: Ovate. Apex: Acute. Margin: Entire. Length:

Approximately 7.0 mm. Width: Approximately 4.0 mm. Texture of upper (inner) surface: Glabrous. Texture of lower (outer) surface: Densely pubescent, hairs appressed. Color of upper (inner) surface: Slightly darker than 144A. Color of lower (outer) surface: 144B.

*Peduncle*.—Strength: Strong, flexible. Aspect: Acute angle to stem. Length: Approximately 1.3 cm. Diameter: Approximately 2.0 mm. Texture: Densely pubescent, hairs appressed. Color: 145B to 145C occasionally tinted with 185A.

*Reproductive organs*.—Androecium: Stamen quantity: 6 to 7, petaloid. Stamen length: Approximately 4.2 cm with 1 to 2 irregularly shaped petaloids attached to base and up to 9.0 mm in length. Filament length: Approximately 4.1 cm. Filament texture: Lower portion densely pubescent with very short colorless glands. Filament color: 47B. Anther shape: Bilobed, dorsifixed. Anther length: Approximately 2.0 mm. Anther color: N34A darkens to 186C with age. Pollen amount: Abundant. Pollen color: NN155A. Gynoecium: Pistil quantity: 1 per flower. Pistil length: Approximately 6.5 cm. Stigma shape: Round, capitate. Stigma length: Approximately 1.0 mm. Stigma color: N167B. Style length: Approximately 6.0 cm. Style color: 47A. Ovary length: Approximately 4.0 mm. Ovary texture: Densely pubescent with long white hairs. Ovary color: N137B.

Seed and fruit production: Neither seed nor fruit production has been observed.

Garden performance and temperature tolerance: Plants of the new Azalea have been observed to be very tolerant to rain, wind and are suitable for USDA Hardiness Zones 7 to 9.

Disease and pest resistance: Resistance to pathogens and pests common to Azalea has not been observed.

What is claimed is:

1. A new and distinct cultivar of Azalea plant named 'Lazamored', substantially as herein illustrated and described.

* * * * *